(12) United States Patent
Liu (10) Patent No.: US 9,497,994 B2
(45) Date of Patent: Nov. 22, 2016

(54) ELECTRONIC CIGARETTE DEVICE, ELECTRONIC CIGARETTE, AND ATOMIZING DEVICE USED IN THE SAME

(71) Applicant: Qiuming Liu, Shenzhen (CN)

(72) Inventor: Qiuming Liu, Shenzhen (CN)

(73) Assignee: HUIZHOU KIMREE TECHNOLOGY CO., LTD., SHENZHEN BRANCH, Shenzhen, Guangdong Province (CN)

( * ) Notice: Subject to any disclaimer, the term of this patent is extended or adjusted under 35 U.S.C. 154(b) by 802 days.

(21) Appl. No.: 13/992,738

(22) PCT Filed: Jan. 5, 2013

(86) PCT No.: PCT/CN2013/070061
§ 371 (c)(1),
(2) Date: Jun. 8, 2013

(87) PCT Pub. No.: WO2014/106329
PCT Pub. Date: Jul. 10, 2014

(65) Prior Publication Data
US 2014/0332019 A1    Nov. 13, 2014

(51) Int. Cl.
| | | |
|---|---|---|
| *A24F 13/00* | (2006.01) | |
| *A24F 47/00* | (2006.01) | |
| *F22B 1/28* | (2006.01) | |
| *A61M 15/06* | (2006.01) | |
| *A61M 11/04* | (2006.01) | |

(Continued)

(52) U.S. Cl.
CPC ........... *A24F 47/008* (2013.01); *A61M 11/042* (2014.02); *A61M 15/06* (2013.01); *F22B 1/284* (2013.01); *A61M 11/044* (2014.02); *A61M 15/0021* (2014.02); *A61M 2016/0024* (2013.01); *A61M 2205/3653* (2013.01); *A61M 2205/8206* (2013.01); *A61M 2209/06* (2013.01)

(58) Field of Classification Search
CPC ............... A24F 47/008; A61M 11/042; A61M 11/044
See application file for complete search history.

(56) References Cited

U.S. PATENT DOCUMENTS

2011/0036346 A1* 2/2011 Cohen ............... A61M 15/0065
128/200.14
2011/0303231 A1* 12/2011 Li ......................... A24F 47/008
131/329

(Continued)

*Primary Examiner* — Alex Efta
(74) *Attorney, Agent, or Firm* — Cheng-Ju Chiang (57) ABSTRACT

An atomizing device comprises an atomizing seat, and an atomizer having a heating wire and disposed at one side of the atomizing seat. A first electrode assembly is disposed at another side of the atomizing seat away from the atomizer. The first electrode assembly includes a first seat body and a first electrode post, two of which two of which are insulated from each other and respectively connected with two ends of the heating wire to form the positive and negative electrode. The first seat body resists the atomizing seat and clamps a first end of the heating wire therebetween, and the first electrode post resists the atomizing seat and clamps a second end of the heating wire therebetween. The heating wire is secured by the squeezing of the atomizing seat and the first electrode assembly, the atomizing sleeve, which has a stable structure and low cost.

12 Claims, 8 Drawing Sheets

(51) Int. Cl.
*A61M 16/00* (2006.01)
*A61M 15/00* (2006.01)

(56) References Cited

U.S. PATENT DOCUMENTS

| | | | |
|---|---|---|---|
| 2012/0260927 A1* | 10/2012 | Liu | A24F 47/008 131/329 |
| 2013/0192617 A1* | 8/2013 | Thompson | A24F 47/008 131/329 |
| 2013/0248385 A1* | 9/2013 | Scatterday | A24F 15/12 206/86 |
| 2013/0255702 A1* | 10/2013 | Griffith, Jr. | A24F 47/008 131/328 |

* cited by examiner

ELECTRONIC CIGARETTE DEVICE, ELECTRONIC CIGARETTE, AND ATOMIZING DEVICE USED IN THE SAME

CROSS REFERENCE TO RELATED APPLICATIONS

The present application is a 35 U.S.C. §371 National Phase conversion of International (PCT) Patent Application No. PCT/CN2013/070061, filed on Jan. 5, 2013, the disclosure of which is incorporated by reference herein. The PCT International Patent Application was filed in Chinese.

FIELD OF THE INVENTION

The present invention relates to electronic cigarettes and electronic cigarette cases, and more particularly pertains to an electronic cigarette and an electronic cigarette device, in which a heating wire of an atomizing device and an electrode assembly is not required to weld, and are secured by mutual squeezing.

BACKGROUND OF THE INVENTION

Current atomizing device in electronic cigarettes generally includes an atomizer having a heating wire disposed therein, an atomizing cup having tobacco flavored liquid therein, an atomizing seat used for fixing the atomizing cup, and an atomizing sleeve sleeved at an outer of the atomizing cup.

Two ends of the heating wire in the electronic cigarette need to be electrically connected to positive and negative electrodes of a battery to supply power source. The heating wire of the electronic cigarette is generally welded to the electrodes of the battery to electrically connect with the battery. Perhaps, an end of the atomizing seat disposes a separate electrode assembly, and two ends of the heating wire are respectively welded to corresponding electrodes of the electrode assembly, thus the electrode assembly electrically connects with the positive and negative electrodes of the battery. Connection by welding is time cost and strenuous, and is also low stability. Further, connection by welding results in bad phenomenon such as rosin joint, tack weld, and produces residue harmful to people.

Owing to the atomizing cup disposing tobacco flavored liquid, the sealing of the atomizing cup need to be guaranteed when making the atomizing cup sleeved in the atomizing sleeve utilizing the atomizing seat. When fixing the atomizing cup utilizing the atomizing seat, absorbent cotton is firstly packaged in the atomizing seat. The outer edge of traditional atomizing seat generally defines groove for latching the absorbent cotton to fix the absorbent cotton. The atomizing seat must be firstly manufactured to form flange by supplier, and then turned outside in after packaging the absorbent cotton, which is complicated. When sealing the atomizing cup, a typical way is to dispose a sealing washer between the atomizing sleeve and the atomizing seat, or to dispense glue at the juncture of the atomizing sleeve and the atomizing seat to form sealing glue layer to achieve the sealing of the atomizing cup. Disposing a separate sealing washer may enhance manufacturing cost, and is difficult to assembly, which is time cost and strenuous. Dispensing glue is unsafe to operate, and is unfriendly environment.

SUMMARY OF THE INVENTION

A problem to be solved by the present invention is to provide an atomizing device of electronic cigarette, in which a heating wire directly connects with electrode assembly not by welding, and has a higher connection stability.

Another problem to be solved by the present invention is to provide an electronic cigarette, in which a heating wire directly connects with electrode assembly not by welding, and has a higher connection stability.

An additional problem to be solved by the present invention is to provide an electronic cigarette device, in which a heating wire directly connects with electrode assembly not by welding, and has a higher connection stability.

To solve the above problems, the present invention provides an atomizing device for an electronic cigarette comprising an atomizing seat, and an atomizer having a heating wire and disposed at one side of the atomizing seat. A first electrode assembly is disposed at another side of the atomizing seat away from the atomizer. The first electrode assembly includes a first seat body and a first electrode post, two of which are insulated from each other and respectively connected with two ends of the heating wire to form the positive and negative electrodes of the atomizer. The first seat body is pressed against the atomizing seat and clamps a first end of the heating wire therebetween. The first electrode post is pressed against the atomizing seat and clamps a second end of the heating wire therebetween.

In a further embodiment, the atomizing seat is made of rubber material.

In a further embodiment, the atomizing seat is made of rubber material.

In a further embodiment, the atomizing seat defines a first line hole and a second line hole respectively for being passed through by the two ends of the heating wire. The first end of the heating wire passes through the first line hole, and is bent into and enters the latching groove. The second end of the heating wire passes through the second line hole, and is bent into and enters the through hole.

In a further embodiment, the atomizing device further comprises an atomizing sleeve. The outer configuration of the atomizing seat mates with the inner configuration of the atomizing sleeve, and is tightly fixed by expansion in the atomizing sleeve by the first electrode assembly.

Further, the present invention provides an electronic cigarette comprising an atomizing device and a battery electrically connected with the atomizing device and supplying power source to the atomizing device. The atomizing device includes an atomizing seat, and an atomizer having a heating wire and disposed at one side of the atomizing seat. A first electrode assembly is disposed at another side of the atomizing seat away from the atomizer. The first electrode assembly includes a first seat body and a first electrode post, two of which are insulated from each other and respectively connected with two ends of the heating wire to form the positive and negative electrode of the atomizer. The first seat body is pressed against the atomizing seat and clamps a first end of the heating wire therebetween. The first electrode post is pressed against the atomizing seat and clamps a second end of the heating wire therebetween. The battery is disposed at the side of the atomizing device having the first electrode assembly.

In a further embodiment, one end of the battery adjoining the atomizing device has a second electrode assembly. The second electrode assembly includes a second seat body and a second electrode post correspondingly connected with the positive and negative electrode of the battery and the atomizer.

In a further embodiment, the second seat body is hollow cylinder, and has an electrode post cavity defined at one end thereof facing the battery. The second post is fixed in the electrode post cavity by an insulation sleeve.

In a further embodiment, the insulation sleeve includes a first insulation bracket and a second insulation bracket, which mates with each other and cooperatively define an inside cavity therein. The second electrode post is elastically disposed in the center of the insulation sleeve by a coil spring located in the inside cavity. The opposite bottom walls of the first insulation bracket and the second insulation bracket respectively define a first electrode hole and a second electrode hole, which all communicate with the inside cavity. The portion of the second electrode post located in the inside cavity has a baffle flange. Two ends of the coil spring respectively resist the baffle flange and an inner wall of the second insulation bracket so as to make the end of the second electrode facing the second electrode assembly keep protrudent state.

In a further embodiment, the second seat body defines a securing groove communicating with the electrode post cavity at one end thereof towards the first seat body such that a corresponding end of the first seat body inserts into the securing groove to fix the first the seat body. The end of the first seat body inserting into the second seat body has a raised stage which mates with the inner configuration of the securing groove to latch in the securing groove.

In a further embodiment, the atomizing sleeve is an inhalation pole. The electronic cigarette further includes a battery pole disposing the battery and coupling with the inhalation pole. The battery pole and the inhalation pole are detachably connected with each other.

In a further embodiment, the inhalation pole disposes a first magnetic portion at the connection area with the battery pole. The battery pole correspondingly disposes a second magnetic portion adsorbing with the first magnetic portion by magnetic force to make the inhalation pole and the battery pole stably coupled with each other.

In a further embodiment, the first seat body is made of conductive magnet or magnetic material to form the first magnetic portion, or the first electrode assembly disposes a separate element made of conductive magnet or magnetic material to form the first magnetic portion, The second seat body is made of conductive magnet or magnetic material to form the first magnetic portion, or the second electrode assembly disposes a separate element made of conductive magnet or magnetic material to form the first magnetic portion.

In a further embodiment, the electronic cigarette further includes an atomization control unit electrically connected with the battery to control the atomizing device turned on or off, The atomization control unit includes an atomization control circuit and an atomization control switch connected with the atomization control circuit, The atomization control switch is a capacitive sensor switch, a pneumatic sensor switch or a key switch. The atomization control circuit is integrated in the atomization control switch, or the atomization control unit further includes an atomization controlling circuit board electrically connected with the battery and the atomization control switch. The atomization circuit is integrated in the atomization controlling circuit board.

Additionally, the present invention further provides an electronic cigarette device. The electronic cigarette device includes at least one electronic cigarette case and at least one electronic cigarette accommodated in the electronic cigarette case. Each electronic cigarette comprises an atomizing device and a battery electrically connected with the atomizing device and supplying power source to the atomizing device. The atomizing device includes an atomizing seat, and an atomizer having a heating wire and disposed at one side of the atomizing seat. A first electrode assembly is disposed at another side of the atomizing seat away from the atomizer. The first electrode assembly includes a first seat body and a first electrode post, two of which are insulated from each other and respectively connected with two ends of the heating wire to form the positive and negative electrodes of the atomizer. The first seat body is pressed against the atomizing seat and clamps a first end of the heating wire therebetween. The first electrode post is pressed against the atomizing seat and clamps a second end of the heating wire therebetween. The battery is disposed at the side of the atomizing device having the first electrode assembly.

The present invention has the following advantage: utilizing the first seat body resisting the atomizing seat to clamp a first end of the heating wire therebetween to achieve a first end the heating wire electrically connected with the first seat body. At the same time, a second end of the heating wire is clamped between the first electrode post and the atomizing seat by utilizing the first electrode post resisting the atomizing seat to achieve the second end of the heating wire electrically connected with the first electrode post, two of which forms the positive and negative electrode of the atomizing device. The present invention has simple structure and high stability.

The components in the drawings are not necessarily drawn to scale, the emphasis instead being placed upon illustrating the principles of the present disclosure. Moreover, in the drawings, like reference numerals designate corresponding parts throughout several views, and all the views are schematic.

DETAILED DESCRIPTION OF THE INVENTION

Referring to FIG. 1 to FIG. 10, an embodiment of the present invention provides an electronic cigarette device comprising an electronic cigarette 100 and an electronic cigarette case 200 for receiving the electronic cigarette 100.

Figure 2:
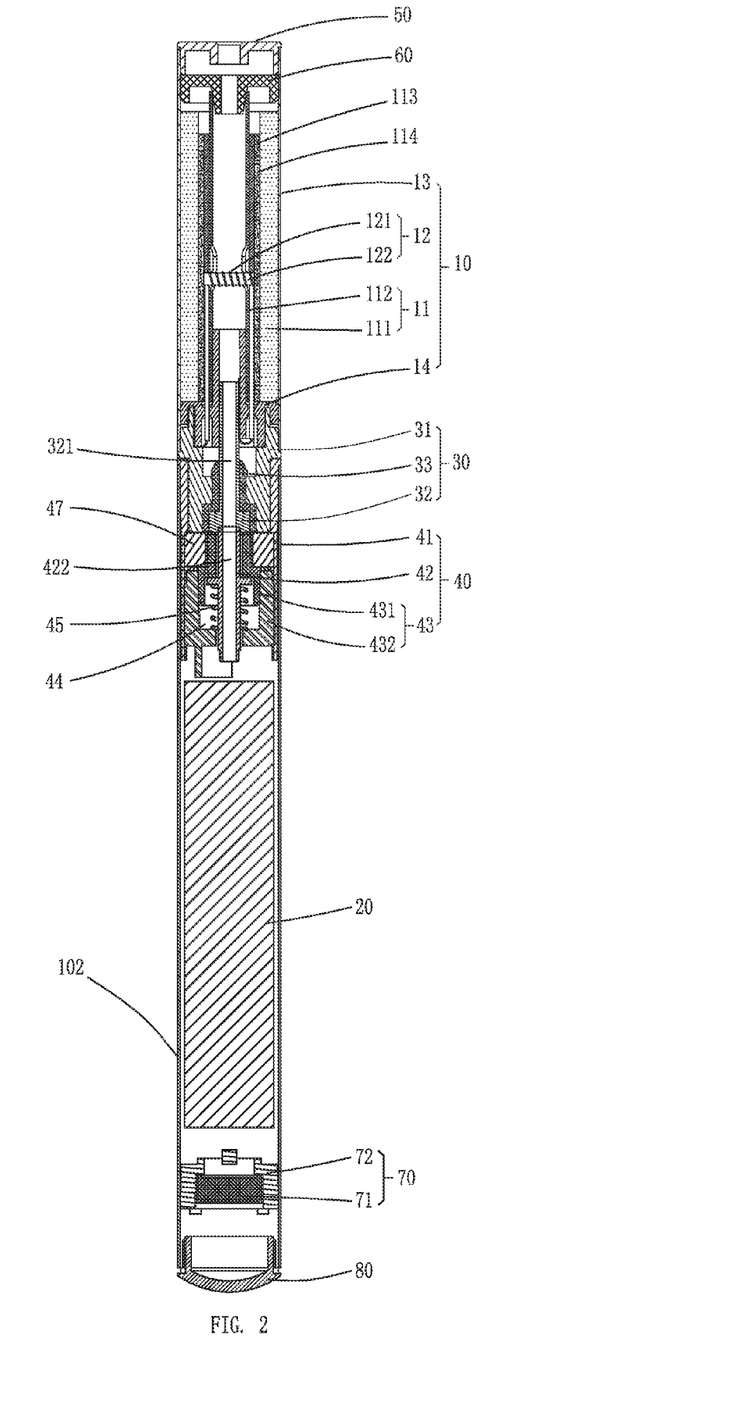
FIG. 2 is a sectional view of the electronic cigarette according to an embodiment of the present invention.

Referring to FIG. 2, the electronic cigarette 100 includes an atomizing device 10 for vaporizing tobacco flavored liquid, and a battery 20 electrically connected with the atomizing device 10 and supplying power source to the atomizing device 10.

The atomizing device 10 includes an atomizing cup 11, an atomizer 12 received and fixed in the atomizing cup 11, an atomizing sleeve 13 sleeved at the outer of the atomizing cup 11, and an atomizing seat 14 located in the atomizing sleeve 13 to secure the atomizing cup 11 and the atomizer 12.

The atomizing cup 11 is used for storage tobacco flavored liquid, and includes a liquid storage element 111 and a supporting tube 112. In this embodiment, the liquid storage element 111, the supporting tube 112, and the atomizing sleeve 13 are all substantially hollow tube structure and are all disposed along a same axis.

The liquid storage element 111 has liquid-absorbing and liquid-storing ability, and used for absorbing and storing tobacco flavored liquid such that the atomizer 12 then vaporizes tobacco flavored liquid. In this embodiment, the liquid storage element 111 may be made of material capable of absorbing liquid and storing liquid such as glass fiber, high-temperature cotton, chemical fiber cotton, cotton mix, liquid-absorbing cotton, nickel foam.

The supporting tube 112 is made of glass fiber. The supporting tube 112 is sleeved in the liquid storage element 111 and used for allowing an airflow to pass through and supporting and fixing for the liquid storage element 111.

The atomizer 12 is used for vaporizing the tobacco flavored liquid into smoke, and includes a heating wire 121 and an atomizing pole 122. The heating wire 121 winds around the atomizing pole 122, and located in the atomizing cup 11 using the atomizing pole 122. In this embodiment, the atomizing pole 122 is column-shaped, and is made of glass fiber material or other high-temperature fiber material for inhaling tobacco flavored liquid, which then is supplied to the heating wire 121 to vaporize.

Figure 4:
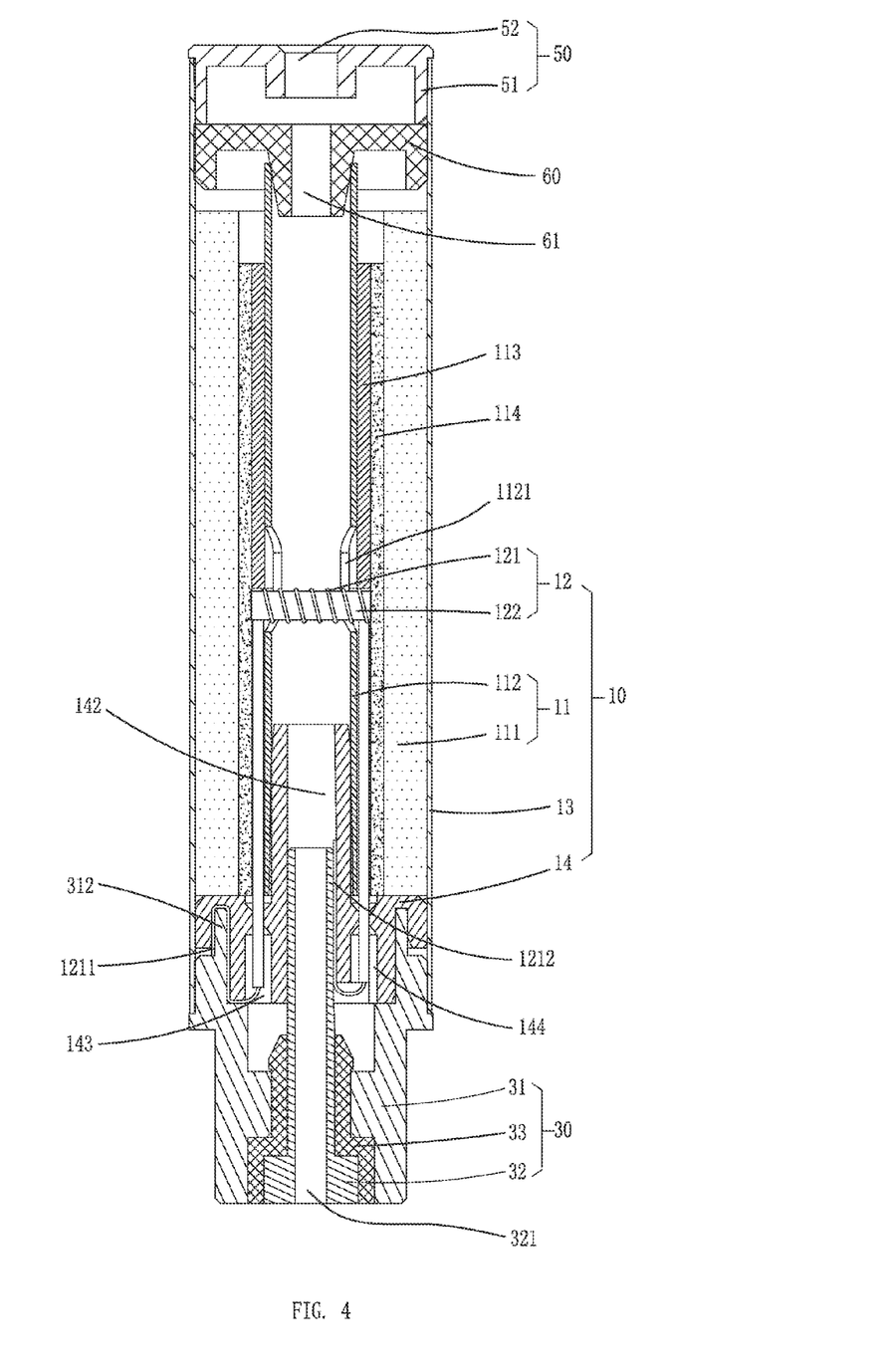
FIG. 4 is a perspective view of the inhalation pole of the electronic cigarette according to an embodiment of the present invention.

Referring to FIG. 4, in this embodiment, the atomizing pole 122 is disposed in the supporting tube 112 along radial direction. Sidewalls of the central portion of the supporting tube 112 have latching openings 1121 along radial direction and communicating through the sidewalls. Two ends of the atomizing pole 122 pass throughout the supporting tube 112 from the latching openings 1121 and resist the inner wall of the liquid storage element 111 so as to inhale tobacco flavored liquid which then is supplied to the heating wire 121 to vaporize. Simultaneously, to avoid the atomizing pole 122 to axially move in the supporting tube 112, the outer of the supporting tube 112 is sleeved around a positioning sleeve 113 located on or under the atomizing pole 122. One end of the positioning sleeve 113 resists on the atomizing pole 122 so as to tightly resist the atomizing pole 122 in the latching openings 1121. In this embodiment, to make the heating wire 121 easily arranged and save space, the positioning sleeve 113 is preferably sleeved on the atomizing pole 122. As one embodiment, the atomizing pole 122 may be axially located in the supporting tube 112. At this time, the heating wire 121 must completely contact with the inner wall of the supporting tube 112 so as to make the inner wall of the supporting tube 112 allow an airflow to pass through.

Referring to FIG. 4, because of the heating wire 121 having higher temperature when being electrified, to enhance working life and hear-resisting performance of the liquid storage element 111, a heat insulation element 114 is sleeved between the liquid storage element 111 and the supporting tube 112 in this embodiment. The heat insulation element 114 is made of material enduring high temperature and having such liquid-absorbing ability, such as high-temperature cotton, or nonwoven fabric and so on.

The atomizing sleeve 13 is sleeved around the liquid storage element 111, the supporting tube 112 and the atomizing seat 14, and provides a cup containing and sealing tobacco flavored liquid for the atomizing device 10. In this embodiment, the atomizing sleeve 13 is a column-shaped tube body, and is hollow to form a receiving cavity for receiving all elements in the atomizing device 10. It is understood that the atomizing sleeve 13 may be any other tube body having hollow cavity, not limited to column-shaped tube body of this embodiment.

Figure 5:
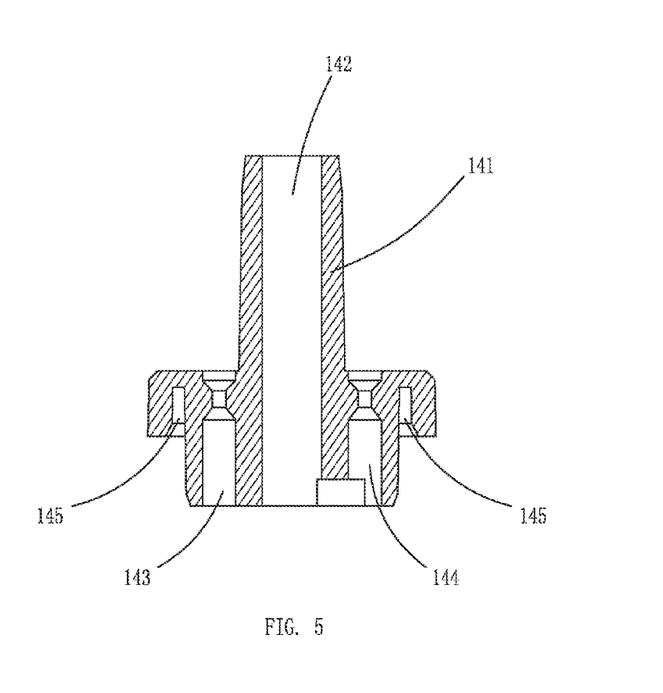
FIG. 5 is a sectional view of the atomizing seat of the electronic cigarette according to an embodiment of the present invention.

The atomizing seat 14 is used to support and fix the atomizing cup 11 and the atomizer 12 in the atomizing sleeve 13. As shown in FIG. 5, the atomizing seat 14 protrudes a positioning post 141 from a center thereof towards the inner of the supporting tube 112. An outer diameter of the positioning post 141 is corresponding to the inner diameter of the supporting tube 112 to support the supporting tube 112. The atomizing seat 14 defines a through hole 142 in the center of the positioning post 141 to allow an airflow to pass through.

Figure 3:
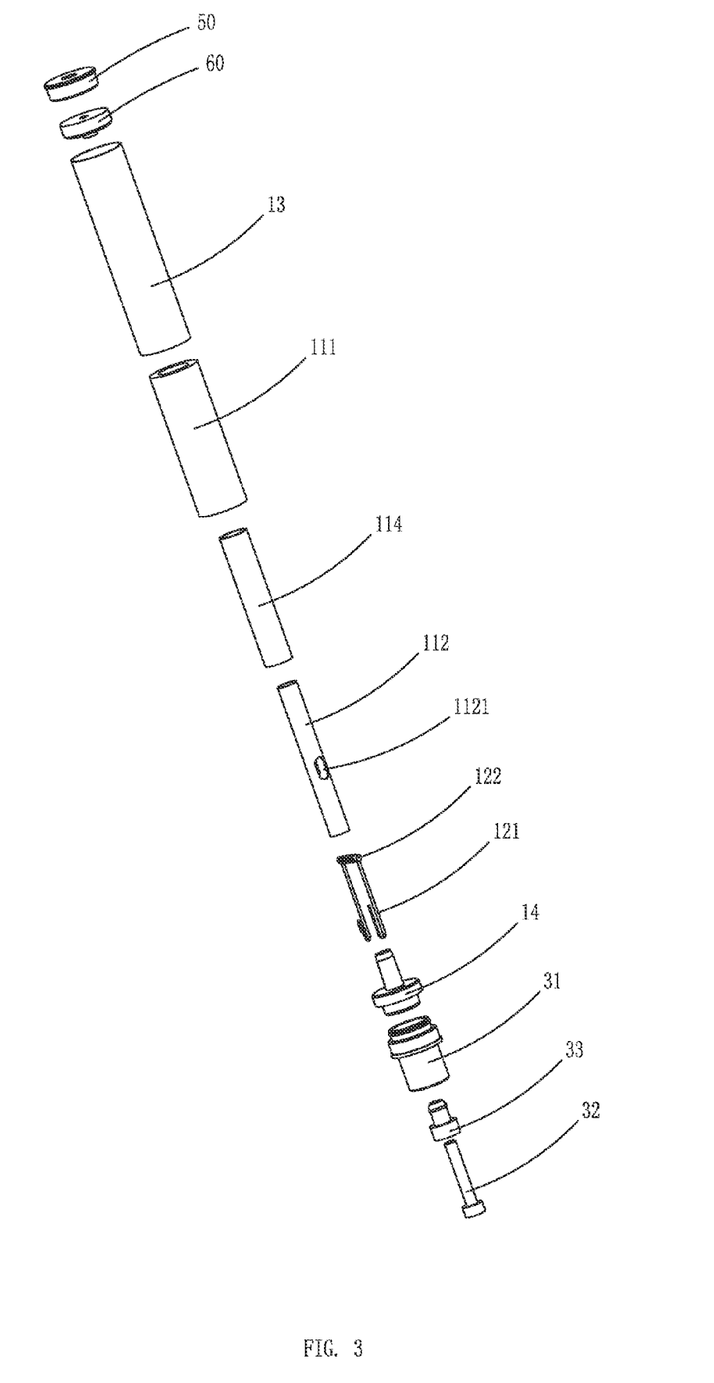
FIG. 3 is a perspective, exploded view of the inhalation pole of the electronic cigarette according to an embodiment of the present invention.

Referring to FIG. 2 to FIG. 4, in this embodiment, a first electrode assembly 30 is disposed at one side of the atomizing seat 14 away from the atomizer 12. The first electrode assembly 30 is configured to be positive and negative electrodes of the atomizing device 10 electrically connected to positive and negative electrode of the battery 20.

Figure 7:
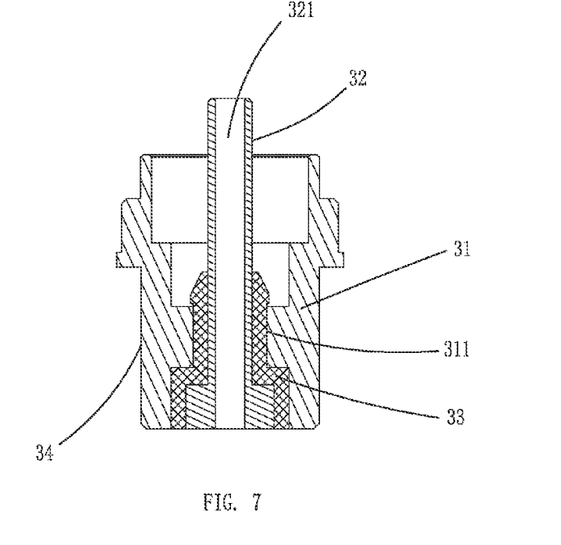
FIG. 7 is a sectional view of the first electrode assembly of the electronic cigarette according to an embodiment of the present invention.

Concretely, as shown in FIG. 4 and FIG. 7, the first electrode assembly 30 includes a first seat body 31, a first electrode post 32, and a first insulation sleeve 33 disposed between the first seat body 31 and the first electrode post 32. The first seat body 31 and the first electrode post 32 are made of metallic conductive material. The first seat body 31 is pressed against the atomizing seat 14 and clamps a first end 1211 of the heating wire 121 therebetween. The first electrode post 32 is pressed against the atomizing seat 14 and clamps a second end 1212 of the heating wire 121 therebetween. Therefore, electrical connection of the heating wire 121 and the first seat body 31, or electrical connection of the heating wire 121 and the first electrode post 32 is achieved to form positive and negative electrode of the atomizing atomizer 12. The first insulation sleeve 33 is made of insulated material to insulate the first seat body 31 and the first electrode post 32.

Figure 6:
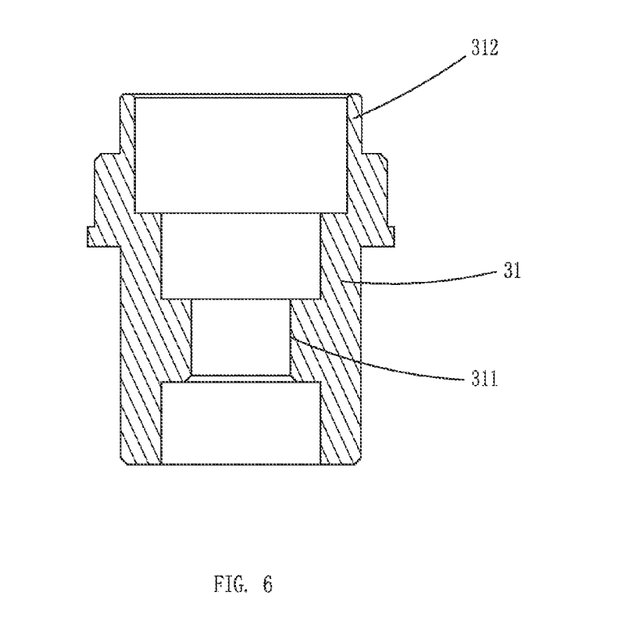
FIG. 6 is a sectional view of the first seat body of the electronic cigarette according to an embodiment of the present invention.

Referring to FIG. 6 and FIG. 7, the first seat body 31 is hollow cylinder, and has a latching ring 311 radially extending from an inner thereof to latch in the first insulation sleeve 33. The first electrode post 32 is configured for matching with the first seat body 31, and latches in and insulates from the first seat body 31 utilizing the first insulation sleeve 33. In this embodiment, the first electrode post 32 is also hollow cylinder, and forms a first inlet hole 321 in the center hollow thereof to make outer air into the atomizing device 10.

Referring to FIG. 5, the atomizing seat 14 axially defines a first line hole 143 and a second line hole 144 respectively for being passed through by the two ends of the heating wire 121. The two ends of the heating wire 121 respectively pass through the first line hole 143 and the second line hole 144, and respectively connect with the first seat body 31 and the first electrode post 32.

In this embodiment, the atomizing seat 14 is made of rubber material having elasticity deformation such as silicon. The atomizing seat 14 matches and securely embeds with the first seat body 31. The two ends of the heating wire 121 is latched between the atomizing seat 14 and the first electrode assembly 30 utilizing the mutual action of the atomizing seat 14 and the first electrode assembly 30. The two ends of the heating wire 121 respectively tightly and securely connects with the first seat body 31 and the first electrode post 32 to achieve connecting with the positive and negative electrode of the battery 20.

Concretely, referring to FIG. 4 and FIG. 7, the atomizing seat 14 defines a latching groove 145 at one end thereof towards the first seat body 31. The first seat body 31 has a latching wall 312 extending towards the latching groove 145 from one end thereof facing the latching groove 145. The latching wall 312 interferingly engages with the latching groove 145. One end of the first electrode post 32 facing the atomizing seat 14 extends into the through hole 142 of the positioning post 141, and interferingly engages with the through hole 142. When assembling the heating wire 121, the first end 1211 of the heating wire 121 passes through the first line hole 143, and is bent into the latching groove 145 to achieve the tightly and securely connection of the heating wire 121 and the first seat body 31 by utilizing the mutual squeezing action of the latching wall 312 and the latching groove 145. Correspondingly, the second end 1211 of the heating wire 121 passes through the second line hole 144, and is bent into the through hole 142 to achieve the tightly and securely connection of the heating wire 121 and the first electrode post 32 by utilizing the mutual squeezing action of the first electrode post 32 and the inner wall of the through hole 142.

At the same, the outer configuration of the atomizing seat 14 mates with the inner configuration of the atomizing sleeve 13, and preferably interferingly engages the inner configuration of the atomizing sleeve 13. With the mutual squeezing action of the atomizing seat 14 and the first electrode assembly 30, the atomizing seat 14 can directly cooperate with the first electrode assembly 30 to tightly fix by expansion in the atomizing sleeve 13 so as to hermetically connect with the atomizing sleeve 13, thus avoiding separately installing sealing element such as sealing ring, which results in higher cost, and bad sealing.

Referring to FIG. 2, the battery 20 is arranged to face to the battery assembly 30. One end of the battery 20 adjoining the battery assembly 30 has a second electrode assembly 40. The second electrode assembly 40 matchingly couples with the first electrode assembly 30 to achieve electrical connection between the battery 20 and the atomizing device 10.

Figure 8:
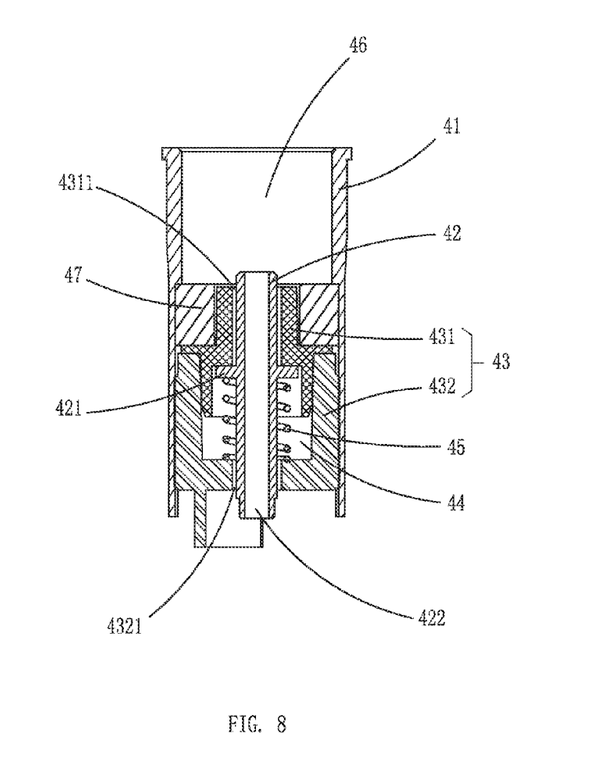
FIG. 8 is sectional view of the second electrode assembly of the electronic cigarette according to an embodiment of the present invention.
Figure 9:
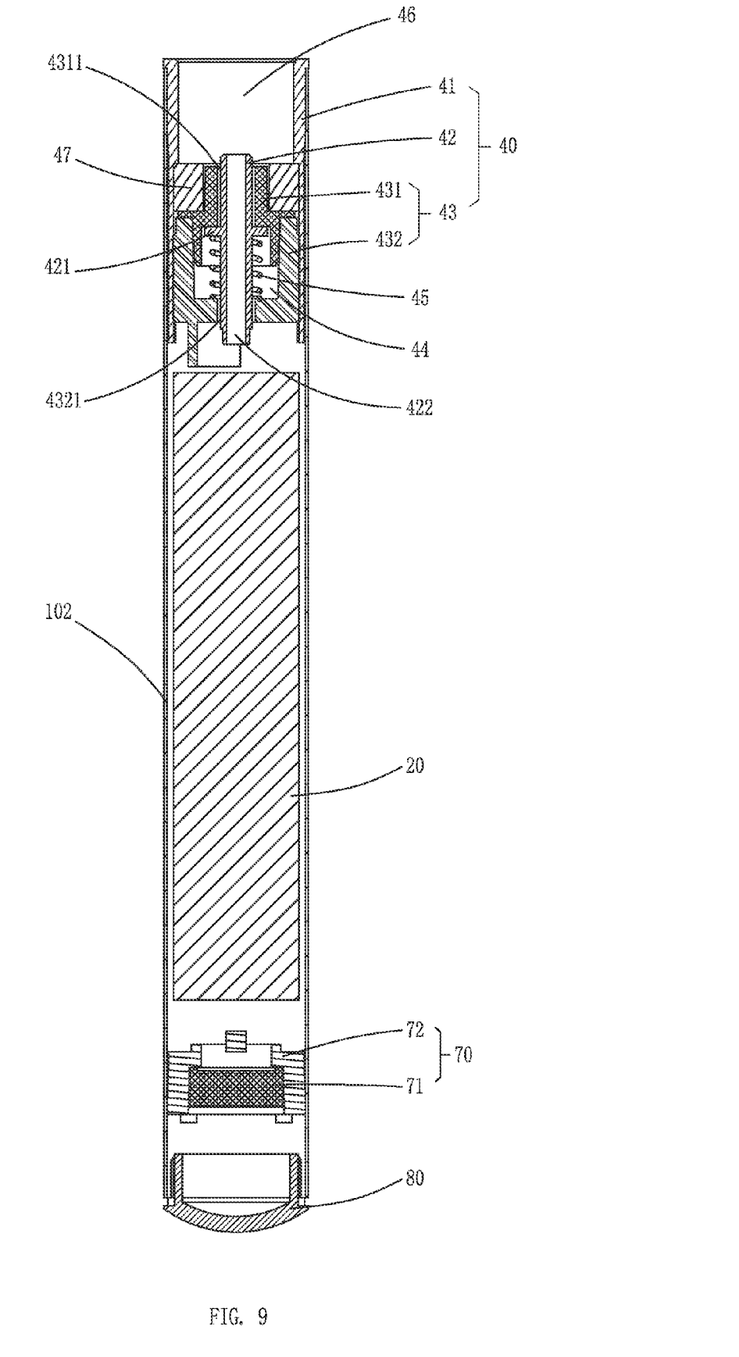
FIG. 9 is sectional view of the battery pole of the electronic cigarette according to an embodiment of the present invention.

Concretely, referring to FIG. 8 and FIG. 9, the second electrode assembly 40 includes a second seat body 41 and a second electrode post 42 correspondingly connected with the positive and negative electrode of the battery 20 and the atomizer 12, and a second insulation sleeve 33 located between the second seat body 41 and the second electrode post 42 to insulate the second seat body 41 and the second electrode post 42.

Referring to FIG. 8, the second seat body 41 is also hollow cylinder, and has an electrode post cavity defined at one end thereof facing the battery 20 and for receiving the second electrode post 42. The second insulation sleeve 33 includes a first insulation bracket 431 and a second insulation bracket 432. The first insulation bracket 431 and the second insulation bracket 432 mates with each other, and are tightly fixed by expansion in the electrode post cavity of the second seat body 42. The first insulation bracket 431 and the second insulation bracket 432 cooperatively defines an inside cavity 44 therein. The second electrode post 42 is elastically disposed in the center of the second insulation sleeve 33 by a coil spring 45 located in the inside cavity 44.

The opposite bottom walls of the first insulation bracket 431 and the second insulation bracket 432 respectively define a first electrode hole 4311 and a second electrode hole 4321, which communicates with the inside cavity 44 and is used for the two ends of the second electrode post 32 passing through. The portion of the second electrode post 42 located in the inside cavity 44 has a baffle flange 421. Two ends of the coil spring 45 respectively resist the baffle flange 421 and an inner wall of the second insulation bracket 432 so as to make the end of the second electrode 42 facing the second electrode assembly 30 keep protrudent state. The second electrode post 42 is also hollow tube structure, and defines a second inlet hole 421 communicating with the first inlet hole 321 to allow an airflow to pass through.

Referring to FIG. 7 and FIG. 8, the second seat body 41 defines a securing groove 46 at one end thereof towards the first seat body 31 such that a corresponding end of the first seat body 31 inserts into the securing groove 46 to fix the first the seat body 31. The end of the first seat body 31 inserting into the second seat body 41 has a raised stage 34. The raised stage 34 mates with the inner configuration of the securing groove 46 to latch in the securing groove 46.

When assembling the electronic cigarette 100, the raised stage 34 is received in the securing groove 46, and the first seat body 31 is pressed against the second seat body 41, and the first electrode post 32 is pressed against the second electrode 42. The second electrode post 42 is resisted by the first electrode post 32 to overcome the elastic force of the coil spring 45, and moves towards the battery 20 and tightly resists between the first electrode post 32 and the battery 20 so as to assure a good contact between the second electrode 42 and the first electrode 32, the battery 20. When the first electrode assembly 30 is separated from the second electrode assembly 40, an outer force acted on the second electrode post 42 is removed, and the coil spring 45 thus drives the second electrode post 42 to restore to its original position.

Figure 1:
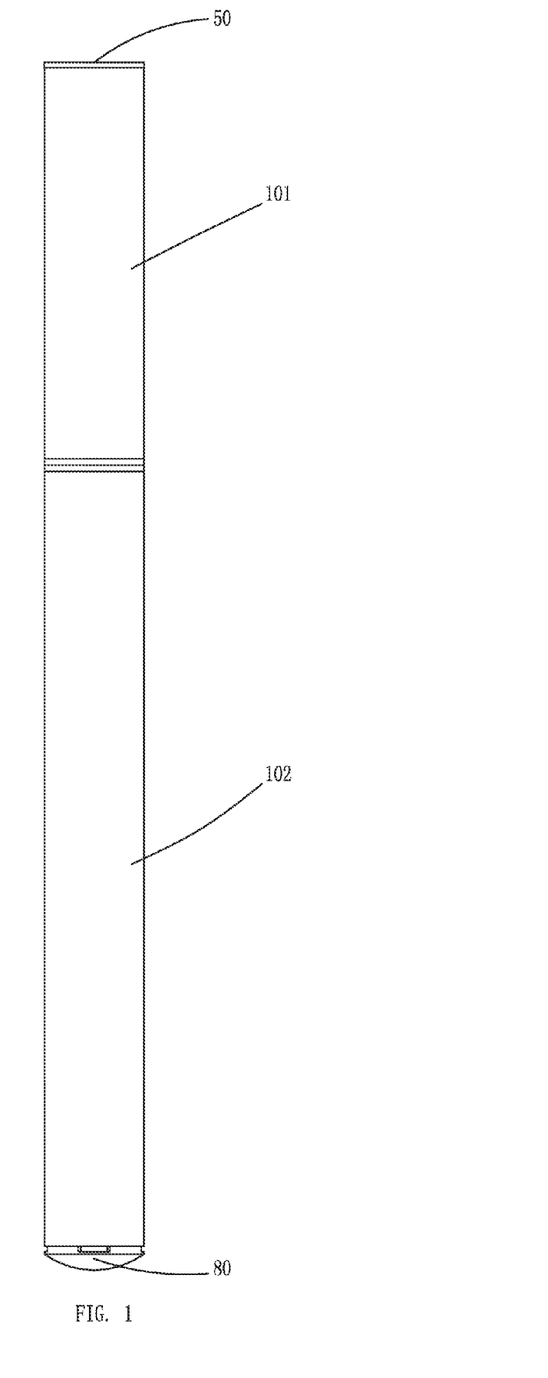
FIG. 1 is a perspective view of the electronic cigarette according to an embodiment of the present invention.

Referring to FIG. 1, the electronic cigarette 100 has an inhalation element 50 disposed at one end thereof away from the battery 20. According to the composition and function of the inner elements in the electronic cigarette 100, the electronic cigarette 100 can be divided into an inhalation pole 101 and a battery pole 102. Generally, the inhalation pole 101 and the battery pole 102 can be detachably connected with each other or undetachably integral structure. When the inhalation pole 101 and the battery pole 102 are detachably connected with each other, the atomizing device 10 is located in the inhalation pole 101 of the electronic cigarette 100, and the inhalation pole 101 may be a separate pole body to entirely accommodate the atomizing device 10. Referring to FIG. 2, the atomizing sleeve 13 may be acted as the pole body of the inhalation pole 101. Perhaps, the e inhalation pole 101 and the battery pole 102 are integrally connected with each other, the atomizing sleeve 13 may be acted as a main pole body of the electronic cigarette 100 such that the battery 20 and the inhalation element 50 are respectively located in the corresponding end of the atomizing sleeve 13.

Referring to FIG. 1 and FIG. 2, in this embodiment, the inhalation pole 101 and the battery pole 102 is detachably connected with each other, and the atomizing sleeve 13 may be acted as the pole body of the inhalation pole 101, in the case of which the electronic cigarette 100 of this embodiment will be further described in the following.

In this embodiment, the atomizing sleeve 13 (namely as the inhalation pole 101) and the battery pole 101 are coupled by magnetic adsorption. Concretely, referring to FIG. 2, the atomizing sleeve 13 disposes a first magnetic portion at the connection area with the battery pole 102, and the battery pole 102 correspondingly disposes a second magnetic portion adsorbing with the first magnetic portion by magnetic force to make the atomizing sleeve 13 and the battery 102 stably coupled with each other.

Because the first electrode assembly 30 is located in the end of the atomizing sleeve 13 adjoining the battery 20, and the second electrode assembly 40 is correspondingly located in the end of the battery 20 adjoining the atomizing device 10, and the first electrode assembly 30 and the second electrode assembly 40 couples with each other, therefore, when disposing the first magnetic portion and the second magnetic portion, to reduce numbers of elements and make the structure of the electronic cigarette 100 simple, the first seat body 31 may be made of conductive magnet or magnetic material to form the first magnetic portion, or the first electrode assembly 30 further disposes a separate element made of conductive magnet or magnetic material to form the first magnetic portion. Correspondingly, the second seat body 41 may be made of conductive magnet or magnetic material to form the first magnetic portion, or the second electrode assembly 40 further disposes a separate element made of conductive magnet or magnetic material to form the first magnetic portion.

Referring to FIG. 2, in this embodiment, the first magnetic portion is comprised of the first seat body 31 made of metallic and conductive material, and the second magnetic portions is comprised of a permanent magnet 47 located in the second seat body 41. Referring to FIG. 8, the permanent magnet 47 is located at the juncture of the electrode post cavity and the securing groove 46, and is circular, and is sleeved in the end of the first insulation bracket 431 adjoining the first seat body 31, and further is insulated from the second electrode post 42 by the first insulation bracket 431.

In this embodiment, the radial width of the electrode post cavity is larger than the radial width of the securing groove 46. Therefore, the juncture of the electrode post cavity and the securing groove 46 forms a flange. The permanent magnet 47 tightly resists at the flange via the first insulation bracket 431.

Referring to FIG. 2, to avoid the first electrode assembly 30 and the second electrode assembly 40 coupling poor to result in a gap between the atomizing sleeve 13 and the battery pole 102 when connecting, it is needed that an axial depth of the securing groove 46 of the second seat body 41 is slightly than an axial height of the raised stage 34 of the first seat body 31 so that when the raised stage 34 is latched in the securing groove 46, there is a gap between the raised stage 34 and the permanent magnet 47 while the raised stage 34 can be adsorb by the permanent magnet 47. Further, there is no gap at the juncture of the atomizing sleeve 13 and the battery pole 102 to make the electronic cigarette more unitary and beautiful.

As one embodiment, the atomizing sleeve 13 and the battery pole 102 may be coupled by threaded connection, latching, or any securing way. For example, the coupling portions of the first seat body 31 and the second seat body 41 respectively disposes an outer screw thread and an inner screw thread engaging with each other to achieve the couple of the atomizing sleeve 13 and the battery pole 102.

Referring to FIG. 2 and FIG. 3, in this embodiment, the inhalation element 50 and the atomizing sleeve 13 are disposed separately. The inhalation element 50 includes an inhalation cover 51 sleeved at end portion of the atomizing sleeve 13, and an inhalation hole 52 axially defined at a center of the inhalation cover 51. As one embodiment, the inhalation element 50 and the atomizing sleeve 30 may be integrally formed. It is understood that the inhalation element 50 may be polygon-shaped, oval-shaped, or any tube-shaped having hollow hole. Perhaps, the inhalation element 50 may be sleeve-shaped structure having a diameter gradually lessening toward the end portion to form a predetermined conical degree.

Referring to FIG. 2 to FIG. 4, a sealing cap 60 is disposed the inhalation element 50 and the atomizing cup 11. The sealing cap 60 defines an air guiding hole 61 at a center thereof for allowing an airflow to pass through. The atomizing cup 11 is hermetically secured in the atomizing sleeve 13 via the atomizing seat 14 and the sealing cap 60.

Referring to FIG. 2 and FIG. 9, the electronic cigarette 100 further includes an atomization control unit 70. The atomization control unit 70 is electrically connected with the battery 20 and the atomizing device 10 to control the atomizing device 10 turned on or off. The atomization control unit 70 may be located between the atomizing device 10 and the battery 20, or be located at one end of the battery 20 away from the atomizing device 10.

In this embodiment, the atomization control unit 70 is preferably located at one end of the battery 20 away from the atomizing device 10. The atomization control unit 70 includes an atomization control circuit and an atomization control switch connected with the atomization control circuit.

In this embodiment, the atomization control switch is a sensor switch 70. The sensor switch 70 is fixed in the battery pole 102 via a switch securing seat 72. Concretely, the sensor switch 70 is a capacitive sensor switch. When using the electronic cigarette 100 to smoke, the capacitance of the capacitive sensor switch changes after induction to inhalation airflow to control the atomization control circuit to connect to a power supply to make the electronic cigarette 100 in a work state. As one embodiment, the sensor switch 70 may be a pneumatic sensor switch. That is, when a user inhales using the inhalation element 50, the cavity of the electronic cigarette 100 produces negative pressure to make the pneumatic sensor switch produce pulsing signal to control the atomization control circuit to connect to a power supply.

Because of the sensor switch 70 is precisely manufactured, the sensor switch 70 generally has a built-in controller. The atomization control circuit of this embodiment may be integrated in the controller of the sensor switch 70. As one embodiment, the atomization control circuit may be integrated in a sensor controlling circuit board separately located at the outer of the sensor switch 70 and electrically connected with the sensor switch 70 and the battery 20.

As one embodiment, the atomization control switch may be a traditional push-button switch. The push-button switch electrically connects with the battery 20 via a push-button controlling circuit board so as to control the atomizing control circuit by operating the push-button to further achieve turning on or off of the circuit of the atomizing device 10.

Referring to FIG. 1, FIG. 2, and FIG. 9, the electronic cigarette 100 disposes a light emitting device at the end thereof away from the inhalation element 50. The light emitting device acts a work indicating lamp, and includes a light emitting unit electrically connected with the battery 20, and a lamp cap 80 located at the corresponding end of the battery pole 102. The lamp cap 80 is used for the light of the light emitting unit projecting out. In this embodiment, the light emitting unit is red light emitting lamp. Therefore, when a user inhales the electronic cigarette 100, the end of the electronic cigarette 100 away from the inhalation element 50 appears red aperture similar to the formation of burning cigarette, which enhances the visual sense authenticity of smokers.

In the following, taking that the end of the battery 20 connected with the second electrode post 42 is positive electrode, and the end of the battery 20 connected with the second seat body 41 is negative electrode, and the atomization control switch is a sensor switch 70 for example, the current flow direction of the electronic cigarette 100 will be detailed described in the following.

When a user inhales the electronic cigarette 100 to smoke, the sensor switch 70 induces to turn-on and connects to the atomizing control circuit, the direction of current is specified that the current reaches the second post 42 from the positive electrode of the battery 20, and enters the positive electrode of the heating wire 121 via the first electrode post 32, and then flows through the negative electrode of the heating wire 121 to reach the first seat body 31, and lastly reaches back to the negative electrode of the battery 20 by the second seat body 41.

It is understood that the electronic cigarette 100 is not limited to embodiments shown in FIG. 1 to FIG. 9. All element limitations can be combined with each other to form new embodiments.

Figure 10:
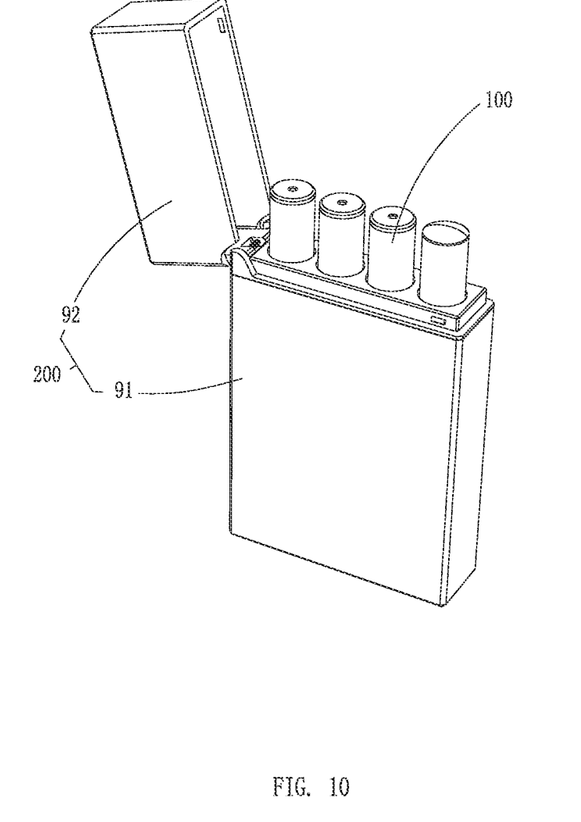
FIG. 10 is perspective view of the electronic cigarette device according to the embodiment of the present invention.

Referring to FIG. 10, the electronic cigarette 100 is generally accommodated in an electronic cigarette case 200. The electronic cigarette case 200 includes a bottom box 91 for accommodating the electronic cigarette 100 and a box cover 92 covering on the bottom box 91. The bottom box 91 is a square case structure, and obviously not limited square, and may be round, oval or polygon-shape as long as the box cover 91 mates with the bottom box 91.

The above-mentioned is embodiments of the present invention. It is pointed out that various improvements and modifications can be made to the embodiments by those skilled in the art without departing from the true spirit and scope of the disclosure as defined by the appended claims.

What is claimed is:

1. An atomizing device for an electronic cigarette, the atomizing device comprising an atomizing seat, and an atomizer having a heating wire and disposed at one side of the atomizing seat, a first electrode assembly being disposed at another side of the atomizing seat away from the atomizer, the first electrode assembly including a first seat body and a first electrode post, both the first seat body and the first electrode post are insulated from each other and respectively connected with two ends of the heating wire to form a positive electrode and a negative electrode of the atomizer, wherein the first seat body is pressed against the atomizing seat and clamps a first end of the heating wire therebetween, and the first electrode post is pressed against the atomizing seat and clamps a second end of the heating wire therebetween;

the atomizing seat defines an axial through hole in a center thereof, and defines a latching groove at one end thereof toward the first electrode assembly; the first electrode post is located in a center of the first seat body, the first seat body has a latching wall extending towards the latching groove from one end thereof and interferingly engages with the latching groove, one end of the first electrode post facing the atomizing seat extends into the through hole of the atomizing seat and interferingly engages with the through hole; the first end of the heating wire enters the latching groove to connect with the first seat body by utilizing a mutual squeezing action of the latching wall and the latching groove, the second end of the heating wire enters the through hole to connect with the first electrode post by utilizing the mutual squeezing action of the first electrode post and an inner wall of the through hole;

the atomizing seat defines a first line hole and a second line hole respectively for being passed through by the two ends of the heating wire, the first end of the heating wire passes through the first line hole, and is bent into and enters the latching groove, the second end of the heating wire passes through the second line hole, and is bent into and enters the through hole.

2. The atomizing device for an electronic cigarette according to claim 1, wherein the atomizing seat is made of rubber material.

3. The atomizing device for an electronic cigarette according to claim 2, wherein the atomizing device further comprises an atomizing sleeve, an outer configuration of the atomizing seat mates with an inner configuration of the atomizing sleeve, and is fixed in the atomizing sleeve by the first electrode assembly.

4. An electronic cigarette, comprising an atomizing device and a battery electrically connected with the atomizing device and supplying power source to the atomizing device, wherein the atomizing device comprises an atomizing seat, and an atomizer having a heating wire and disposed at one side of the atomizing seat, a first electrode assembly disposed at another side of the atomizing seat away from the atomizer; the first electrode assembly includes a first seat body and a first electrode post; the first seat body and the first electrode post are insulated from each other, and respectively connected with two ends of the heating wire to form a positive electrode and a negative electrode of the atomizer; the first seat body is pressed against the atomizing seat and clamps a first end of the heating wire therebetween, and the first electrode post is pressed against the atomizing seat and clamps a second end of the heating wire therebetween, the battery is disposed at the side of the atomizing device having the first electrode assembly;

one end of the battery adjoining the atomizing device has a second electrode assembly, the second electrode assembly includes a second seat body and a second electrode post correspondingly connected with the positive and negative electrode of the battery and the atomizer;

the second seat body is a hollow cylinder, and has an electrode post cavity defined at one end thereof facing the battery, the second post is fixed in the electrode post cavity by an insulation sleeve;

the insulation sleeve includes a first insulation bracket and a second insulation bracket, which mates with each other and cooperatively define an inside cavity therein, the second electrode post is elastically disposed in a center of the insulation sleeve by a coil spring located in the inside cavity, opposite bottom walls of the first insulation bracket and the second insulation bracket respectively define a first electrode hole and a second electrode hole, which all communicate with the inside cavity; a portion of the second electrode post located in the inside cavity has a baffle flange, two ends of the coil spring respectively resist the baffle flange and an inner wall of the second insulation bracket so as to make an end of the second electrode facing the second electrode assembly protrude from the insulation sleeve.

5. The electronic cigarette according to claim 4, wherein the second seat body defines a securing groove communicating with the electrode post cavity at one end thereof towards the first seat body such that a corresponding end of the first seat body inserts into the securing groove to fix the first seat body; the end of the first seat body inserting into the second seat body has a raised stage which mates with the inner configuration of the securing groove to latch in the securing groove.

6. The electronic cigarette according to claim 4, wherein the electronic cigarette further includes a battery pole disposing the battery and coupling with an inhalation pole, the battery pole and the inhalation pole are detachably connected with each other.

7. The electronic cigarette according to claim 6, wherein the inhalation pole disposes a first magnetic portion at the connection area with the battery pole, and the battery pole correspondingly disposes a second magnetic portion adsorbing with the first magnetic portion by magnetic force to make the inhalation pole and the battery pole coupled with each other.

8. The electronic cigarette according to claim 7, wherein the first seat body is made of conductive magnet or magnetic material to form the first magnetic portion, or the first electrode assembly disposes a separate element made of conductive magnet or magnetic material to form the first magnetic portion; the second seat body is made of conductive magnet or magnetic material to form the first magnetic portion, or the second electrode assembly disposes a separate element made of conductive magnet or magnetic material to form the first magnetic portion.

9. The electronic cigarette according to claim 4, wherein the electronic cigarette further includes an atomization control unit electrically connected with the battery to control the atomizing device by turning the electronic cigarette on or off; the atomization control unit includes an atomization control circuit and an atomization control switch connected with the atomization control circuit; the atomization control switch is a capacitive sensor switch, a pneumatic sensor switch or a push-button switch; the atomization control circuit is integrated in the atomization control switch, or the atomization control unit further includes a atomization controlling circuit board electrically connected with the battery and the atomization control switch, the atomization circuit is integrated in the atomization controlling circuit board.

10. An electronic cigarette, comprising an electronic cigarette case and at least one electronic cigarette accommodated in the electronic cigarette case, wherein each electronic cigarette comprises an atomizing device and an battery electrically connected with the atomizing device and supplying power source to the atomizing device; the atomizing device comprising an atomizing seat, and an atomizer having a heating wire and disposed at one side of the atomizing seat, a first electrode assembly being disposed at another side of the atomizing seat away from the atomizer, the first electrode assembly including a first seat body and a first electrode post, the first seat body and the first electrode post being insulated from each other, and respectively connected with two ends of the heating wire to form a positive electrode and a negative electrode of the atomizer, wherein the first seat body is pressed against the atomizing seat and clamps a first end of the heating wire therebetween, and the first electrode post is pressed against the atomizing seat and clamps a second end of the heating wire therebetween, the battery is disposed at the side of the atomizing device having the first electrode assembly;

one end of the battery adjoining the atomizing device has a second electrode assembly, the second electrode assembly includes a second seat body and a second electrode post correspondingly connected with the positive and negative electrode of the battery and the atomizer;

the second seat body is a hollow cylinder, and has an electrode post cavity defined at one end thereof facing the battery, the second post is fixed in the electrode post cavity by an insulation sleeve;

the insulation sleeve includes a first insulation bracket and a second insulation bracket, which mates with each other and cooperatively define an inside cavity therein, the second electrode post is elastically disposed in a center of the insulation sleeve by a coil spring located in the inside cavity, opposite bottom walls of the first insulation bracket and the second insulation bracket respectively define a first electrode hole and a second electrode hole, which all communicate with the inside cavity; a portion of the second electrode post located in the inside cavity has a baffle flange, two ends of the coil spring respectively resist the baffle flange and an inner wall of the second insulation bracket so as to make an end of the second electrode facing the second electrode assembly protrude from the insulation sleeve.

11. The electronic cigarette according to claim 10, wherein the second seat body defines a securing groove communicating with the electrode post cavity at one end thereof towards the first seat body such that a corresponding end of the first seat body inserts into the securing groove to fix the first seat body; the end of the first seat body inserting into the second seat body has a raised stage which mates with the inner configuration of the securing groove to latch in the securing groove.

12. The electronic cigarette according to claim 10, wherein the electronic cigarette further includes a battery pole disposing the battery and coupling with an inhalation pole, the battery pole and the inhalation pole are detachably connected with each other.

* * * * *